US009557216B2

(12) United States Patent
Buckley et al.

(10) Patent No.: US 9,557,216 B2
(45) Date of Patent: Jan. 31, 2017

(54) HIGH SPEED SPECTROSCOPIC SENSOR ASSEMBLY AND SYSTEM

(71) Applicant: TSI, Inc., St. Paul, MN (US)

(72) Inventors: Steven G. Buckley, Redmond, WA (US); Kenneth R. Farmer, Lake Elmo, MN (US); Darrick L. Niccum, Vadnais Heights, MN (US)

(73) Assignee: TSI, INCORPORATED, St. Paul, MN (US)

( * ) Notice: Subject to any disclaimer, the term of this patent is extended or adjusted under 35 U.S.C. 154(b) by 0 days.

(21) Appl. No.: 14/909,213

(22) PCT Filed: Jul. 31, 2014

(86) PCT No.: PCT/US2014/049062
§ 371 (c)(1),
(2) Date: Feb. 1, 2016

(87) PCT Pub. No.: WO2015/017623
PCT Pub. Date: Feb. 5, 2015

(65) Prior Publication Data
US 2016/0178434 A1 Jun. 23, 2016

Related U.S. Application Data

(60) Provisional application No. 61/861,846, filed on Aug. 2, 2013.

(51) Int. Cl.
*G01N 21/00* (2006.01)
*G01J 3/02* (2006.01)
(Continued)

(52) U.S. Cl.
CPC ............. *G01J 3/0275* (2013.01); *B07C 5/342* (2013.01); *G01D 5/26* (2013.01); *G01D 5/48* (2013.01);
(Continued)

(58) Field of Classification Search
CPC ............... G01J 3/02; G01J 3/12; G01J 3/443; G01D 5/26; G01D 5/48; G01N 21/64; G01N 21/68; H01J 37/3293
See application file for complete search history.

(56) References Cited

U.S. PATENT DOCUMENTS 6,061,641 A    5/2000 Hahn et al.
6,795,179 B2   9/2004 Kumar
(Continued)

OTHER PUBLICATIONS

International Search Report from International Application No. PCT/US2014/049062, mailed Jan. 12, 2015 (5 pages).
(Continued)

*Primary Examiner* — Abdullahi Nur
(74) *Attorney, Agent, or Firm* — Kagan Binder, PLLC

(57) ABSTRACT

A laser-based spectroscopy system that combines a distance/proximity standoff sensor, a high-repetition rate laser spectroscopy system, and software with a decision-making algorithm embedded in a processing unit which in combination performs selective firing of the laser when the target object is within an interrogation zone. In a related embodiment, the system provides selective sorting of spectroscopic signals based on information from the standoff signal and from information contained in the spectral signals themselves. The laser emission can be actively controlled while keeping the laser firing, thereby preserving the thermal stability and hence the power of the laser; and the standoff sensor information and the spectral information can be combined to determine the proper relative weighting or importance of each piece of spectral information.

20 Claims, 2 Drawing Sheets

(51) Int. Cl.
- *B07C 5/342* (2006.01)
- *G01J 3/443* (2006.01)
- *G01N 21/71* (2006.01)
- *G01D 5/26* (2006.01)
- *G01D 5/48* (2006.01)
- *G01J 3/12* (2006.01)

(52) U.S. Cl.
CPC ............ *G01J 3/0248* (2013.01); *G01J 3/0289* (2013.01); *G01J 3/12* (2013.01); *G01J 3/443* (2013.01); *G01N 21/718* (2013.01)

(56) References Cited

U.S. PATENT DOCUMENTS

| | | |
|---|---|---|
| 8,476,545 B2 | 7/2013 | Sommer et al. |
| 8,780,347 B2 * | 7/2014 | Kotidis .................. B82Y 20/00 356/364 |
| 2013/0056398 A1 | 3/2013 | Adams et al. |

OTHER PUBLICATIONS

Written Opinion from International Application No. PCT/US2014/049062, mailed Jan. 12, 2015 (7 pages).

International Preliminary Report on Patentability from International Application No. PCT/US2014/049062, mailed Feb. 2, 2016 (8 pages).

* cited by examiner

HIGH SPEED SPECTROSCOPIC SENSOR ASSEMBLY AND SYSTEM

CLAIM OF PRIORITY

This application claims priority to International Application No. PCT/US2014/49062, filed Jul. 31, 2014, and titled "HIGH SPEED SPECTROSCOPIC SENSOR ASSEMBLY AND SYSTEM", which in turn claims priority from U.S. Provisional Patent Application No. 61/861,846, filed Aug. 2, 2013 and titled "HIGH SPEED INDUSTRIAL SPECTROSCOPIC SENSOR", both of which are incorporated herein by reference in their entireties.

FIELD OF THE INVENTION

The invention relates generally to spectroscopic sensing, and more particularly to a high speed, high repetition rate laser spectroscopy system.

BACKGROUND OF THE INVENTION

Quantitative measurements of manufactured products for quality control purposes can be difficult in high speed operations, such as when a target material is being conveyed at varying or high rates of speed, and/or the target material itself varies in one or more dimensions or characteristics. Often times, off-line testing is employed, such as complex laboratory testing and/or test methods, which can be time-consuming, and can result in significant amount of nonconforming product to be made before it is recognized that the process needs adjusting to make conforming product.

Online sensing and analysis offers the advantage of testing in real-time such that process parameters can be quickly and efficiently adjusted so that the target material is in conformance for a greater percentage of the manufacturing run, resulting in less waste and lower cost. Online sensing can be accomplished, for example, via laser spectroscopy. However, problems arise when the target material, i.e. the material to be measured, has motion relative to a laser focal point. U.S. Pat. No. 6,061,641 to Hahn is directed to an algorithm-based analysis of a spectral signal from a randomly-firing laser to determine whether the target was "hit" or not. Commercially available products are available that incorporate distance sensors for spectroscopic measurements. However, there remains a need for a laser-based spectroscopy system designed to solve the problem of performing laser-based spectroscopic measurements on a target item that has motion relative to a laser focal point or a measurement zone.

SUMMARY OF THE INVENTION

Various embodiments of the invention are designed to solve the problem of performing laser-based spectroscopic measurements on a target item or material that has motion relative to a laser focal point. This problem may be encountered (for example) either with a moving conveyor conveying target material with varying depth, or with a conveyed sensor or detector moving over a target such as the ground, which has variation in height.

Various embodiments of the invention are directed to a laser-based spectroscopy system that combines a distance/proximity/standoff sensor assembly or detector, a high-repetition rate laser spectroscopy system, and a processing unit that includes a decision-making algorithm or logic as part of the software program that provides for selectively firing of the laser when the surface of the target material or object or particle is in the focal region of the laser and the collection optics as the target object is moving past or relative to an interrogation zone. In a related embodiment, the target object may be stationary and have a moving laser assembly and/or standoff sensor that moves relative to the target object. The aforementioned combination, in a related embodiment, also provides for selective sorting of spectroscopic signals based on information from a standoff signal from the standoff sensor assembly and from information contained in the spectral signals themselves received from the target object being sampled.

Advantages to the various embodiments and to the methods described herein include: 1) the laser firing or emission can be controlled to allow for selective firing, thereby increasing the laser lifetime and obtaining improved spectra data on each laser shot (as only the laser is triggered when the target object is detected by the standoff sensor to be in the best location within the interrogation zone); 2) the number of times a laser is firing within a period of time can be actively controlled while maintaining the laser in continuous firing mode, for instance to keep pace with the moving target objects or depending on the density of objects traveling through the interrogation zone (low or high density, thereby preserving the thermal stability and hence the power of the laser; and 3) the standoff sensor or detector assembly information and the collected spectral information can be combined to determine the proper relative weighting (importance) of each piece of spectral information collected from the targeted samples.

In one example embodiment, a system is provided for performing laser-based spectroscopic measurements on one or more moving objects within an interrogation zone that includes a laser-based sensor assembly configured to direct a laser light to at least one moving object within the interrogation zone with the laser-based sensor assembly further adapted to receive a portion of a set of spectroscopic signals from the at least one moving object. The system also includes a position sensor assembly for detecting a position of the at least one moving object within the interrogation zone and for generating position data from the at least one moving object located within the interrogation zone. The system further includes a processing unit adapted to receive the set of spectroscopic signals from the laser-based sensor assembly and adapted to receive position data from the position sensor assembly, the processing unit including decision logic therein configured to use the position data to perform selective sorting of the spectroscopic signals received from the at least one moving object. In a related embodiment, the set of spectroscopic signals are collected when the object is within the interrogation zone or are collected from the object and then are weighted as a function of the location of the object within the interrogation zone.

In another example embodiment, a system is provided for performing laser-based spectroscopic measurements on one or more moving target objects within an interrogation zone that includes a laser-based sensor assembly configured to direct a laser light through a focusing lens to at least one moving object within the interrogation zone, with the laser-based sensor assembly further including a detector assembly adapted to receive a first portion of a set of spectroscopic signals from the at least one moving target object. The system also includes a position sensor assembly for detecting a position of the at least one moving target object within the interrogation zone and for generating position data from the at least one moving target object within the interrogation zone, the position sensor assembly including a set of lenses adapted to receive and direct a second portion and a third portion of the set of spectroscopic signals to an image sensor array. The system further includes a beamsplitter lens member adapted to direct the first portion of the set of spectroscopic signals to the detector assembly, the beamsplitter member further adapted to direct the second and third portions of the set of spectroscopic signals to the lenses and the image sensor array of the position sensor assembly, wherein the second and third portions of the set of spectroscopic signals move toward a center of the image sensor array when the target object moves away from the focusing lens, and wherein the second and third portions of spectroscopic signals move away from the center of the image array when the target object moves closer to the focusing lens.

In yet another example embodiment, a system is provided for performing laser-based spectroscopic measurements on one or more moving objects within an interrogation zone that includes a laser-based sensor assembly configured to direct a laser light to at least one moving object within the interrogation zone, with the laser-based sensor assembly further adapted to receive a portion of a set of spectroscopic signals from the at least one moving object upon contact with the laser light. The system also includes a position sensor assembly for detecting a position of the at least one moving object within the interrogation zone and for generating position data from the at least one moving object located within the interrogation zone. The system further includes a processing unit adapted to receive the position data from the position sensor assembly and adapted to trigger firing of the laser light at the moving object when a decision logic of the processing unit determines from the position data that the moving object is within the interrogation zone. In this example embodiment, the laser-based sensor assembly is adapted to receive the portion of a set of spectroscopic signals from the at least one moving object after the laser light is fired. In a related embodiment, the moving objects within the interrogation zone include moving the laser-based sensor assembly and interrogation zone relative to the object to be sampled.

The above summary of the invention is not intended to describe each illustrated embodiment or every implementation of the invention. The figures and the detailed description that follow more particularly exemplify these embodiments.

DESCRIPTION OF THE DRAWINGS

The embodiments of the present invention may be more completely understood in consideration of the following detailed description of various embodiments in connection with the accompanying drawings, in which.

Figure 1:
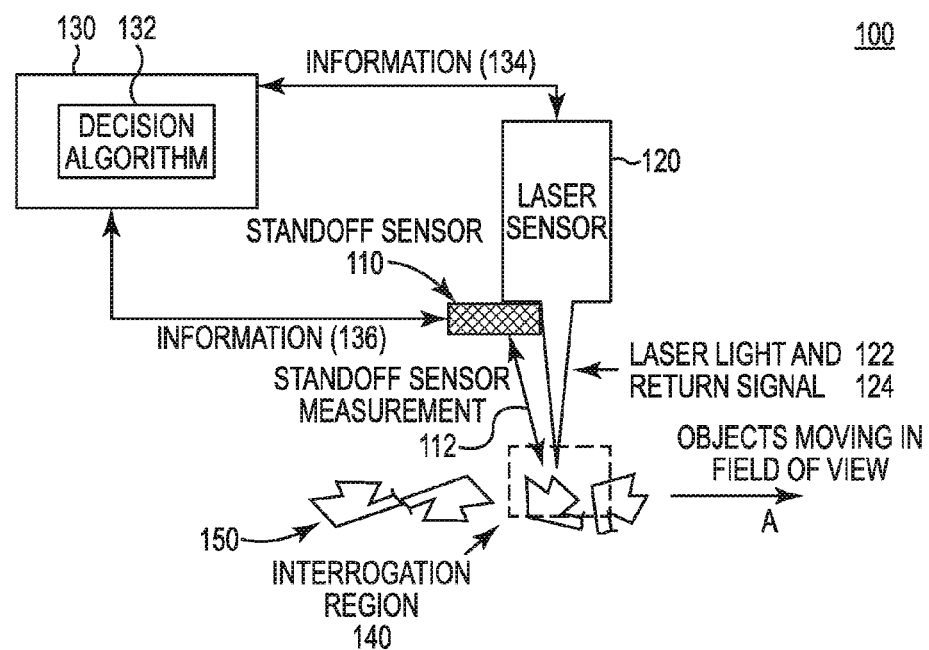
FIG. 1 depicts a high level block diagram of an example embodiment of a laser-based spectroscopy system according to the teachings herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Various embodiments of the invention combine a distance/proximity/standoff sensor assembly, a high-repetition rate laser spectroscopy sensor assembly and a decision-making algorithm or logic embodied in software in a processing unit that collectively or in combination provides for selectively firing of the laser when the surface of the target material or object is in the focal region of the laser and the collection optics as the target object is moving past or relative to an interrogation zone. In a related embodiment, the aforementioned combination provides or performs selective sorting of spectroscopic signals based on information from a standoff sensor signal received from a moving object sample and from information contained in a set of spectral signals themselves of the moving object collected from a laser sensor assembly. The spectroscopic signals can be used to measure, for example, chemical concentrations or compositions, the presence or not of a target component or element, surface topography, temperature, or any of a variety of Characteristics or properties of a target material measured via laser spectroscopy.

There are various methods taught herein for using the sensing systems in various applications. In one example embodiment, the standoff sensor assembly is used to determine when to fire the Q-switch of a high-repetition rate laser of the laser sensor assembly. The diode pump of the laser runs freely at a high (e.g. >20 Hz) fixed rate to optimize the thermal performance of the laser. The standoff (position, proximity, or distance) sensor assembly determines time periods during which there is an object of interest in the target area, and it generates a signal corresponding to position of the target object in the interrogation area or zone. The decision-making algorithm or logic within the processing unit uses the information from the standoff sensor signal to determine time periods during which the Q-switch of the laser should be firing. The firing of the Q-switch then allows spectroscopic signals to be acquired only when an object or particle is in the target area.

Operating the laser at its full repetition rate and acquiring spectroscopic data at full speed, and combining the information from the standoff sensor and the spectroscopic signal(s) allows the user to interpret the quality of the spectroscopic information. For example, a relative "voting" mechanism could be used to weight the importance of each spectrum or emission signal obtained, based on (or as a function of) the proximity or location of the target to the optimal position within the interrogation zone.

According to a non-limiting embodiment depicted in FIG. 1, a high speed, high repetition rate laser spectroscopy system 100 generally includes a standoff or position sensor assembly 110, a laser-based sensor assembly 120, and a processing unit 130 included therein a software program 132 comprising a decision algorithm or logic. Laser-based sensor assembly 120 is configured to fire laser light and to receive light signals from a target object that it strikes or makes contact with. The return light includes a set of spectroscopic signals that are later processed by a spectrometer or spectral analyzer. Processing unit 130 includes a bidirectional communication line 134 coupled to laser assembly 120 and a bidirectional communication line 136 coupled to standoff sensor 110. Standoff or position sensor 110 determines the height of objects moving in the field of view (or interrogation zone) under laser sensor 120. In this example embodiment, the standoff sensor regularly sends position data of detected objects to processing unit 130. Processing unit 130 and software 132 use the position data to determine whether an object is within the field of view of the laser collection optics and, in one example embodiment, uses a weighting factor on the received position data. This weighting factor could be from "zero" to "one"—i.e. no importance to full importance. Assembly 110 and processing unit 130 determine a height of material pieces 150 passing through an interrogation region or zone 140 under laser-based sensor assembly 120. When the target object is in the most efficient location within the interrogation zone, processing unit 130 triggers the laser in laser assembly 110 to fire at the target object. The spectral signals that are collected at that moment are considered to be of high quality as the laser light is striking the object when the object is the best position or location within the interrogation zone, as verified by position data generated by the standoff sensor and processed by processing unit 130.

In one particular embodiment, the laser has significantly higher energy output (320 mJ) than required to generate LIBS spectra thus providing headroom if on-line measurements require it. In this example embodiment, laser sensor assembly 120 uses LIBS (laser induced breakdown spectroscopy) technology, but it is not necessarily limited to same. Laser Induced Breakdown Spectroscopy (LIBS) is a rapid chemical analysis technology that uses a short laser pulse to create a micro-plasma on the sample surface. This analytical technique offers many compelling advantages compared to other elemental analysis techniques including a sample preparation-free measurement experience, extremely fast measurement time, usually a few seconds, for a single spot analysis, broad elemental coverage, including lighter elements, such as H, Be, Li, C, N, O, Na, and Mg, versatile sampling protocols that include fast raster of the sample surface and depth profiling, and thin-sample analysis without the worry of the substrate interference. A typical detection limit of LIBS for heavy metallic elements is in the low-PPM range. LIBS is applicable to a wide range of target materials that include metals, semiconductors, glasses, biological tissues, insulators, plastics, soils, plants, soils, thin-paint coating, food products, and electronic materials. One such system for performing LIBS is commercially available as ChemReveal® from TSI, Inc. See, for example, http://www.tsi.com/chemreveal-libs-desktop-analyzed, which is incorporated herein by reference in its entirety.

In this example embodiment, laser sensor assembly 120 is configured to emit a laser light 122 into interrogation region 140 for material pieces 150 to be analyzed as they move in a direction A (arrow) along a conveyor belt or moving through an angled chute or a tube via gravity. A return light signal 124 is detected by laser sensor assembly 120. The laser sensor assembly 120 is a high repetition rate laser that can either be: 1) configured to selectively fire based on the output of the decision algorithm of processing unit 130 and the position data provided on a target object nearing or in the interrogation zone, thereby increasing laser lifetimes; or 2) configured to fire continuously where the target objects are very close together and/or material sorting is desired.

In another example embodiment of continuous laser firing, the information from standoff sensor 110 is used to weight the importance of return signal 124 from laser sensor assembly 120. In this way a continuous weighted signal could be derived and form an output from processing unit 130 (after it is processed by the decision algorithm or logic).

In the example embodiment of selective firing of the laser sensor assembly, an output 112 from standoff sensor 110 could be used by processing unit 130 (and the decision algorithm program) to selectively fire the laser if a target object (such as a material piece 150) was detected within a particular distance range tolerance. In this example embodiment, only selected pulses from the laser pump (flashlamp or diodes, for example) of laser assembly 120 would form a series of laser pulses. Signals from these laser pulses would all be counted equally, or could be further weighted by the decision algorithm based on the standoff sensor output.

In various example embodiments, various advantages of laser sensor system 100 include: 1) an accurate spectral signal is obtained by properly counting only the spectral information obtained when a target is properly in a distance range of the standoff sensor, and 2) the laser pump is able to keep running at its high (rated) speed, which enhances the thermal stability and energy of the laser. System 100, in this example embodiment, further provides for increased sample frequency, sample size, and sample processing time. With such a sensing system, virtually every target can be measured if desired. Increased sample frequency and/or sample size can result in potentially greater processing (and therefore quality control), reduced product variability and reduced waste.

In one example embodiment, the maximum firing repetition rate of 110 Hz is anticipated to be more than required if every shot results in useable spectra. The laser lifetime warranty is usually about 10,000 hours at the maximum repetition rate of 110 Hz. This equates to $4 \times 10^9$ laser shots before a pump diode replacement is required. This is an 80 times increase in lifetime compared to the specified flash lamp pumped lifetime of $50 \times 10^6$ shots. This is expected to significantly increase system uptime and decrease cost of ownership. Further, in order to minimize the number of laser shots into "empty" space, the standoff or position or distance sensor is used to provide a trigger signal to initiate a laser pulse when a target material surface is located within the measurement zone or the interrogation region. This approach greatly extends the laser operating lifetime and increases the probability of obtaining a quality spectrum from each laser shot.

In a related embodiment, an off-axis collection optics configuration is used. An alternative approach is to use on-axis collection of the LIBS signal, which should improve signal collection efficiency. Another feature (not shown) that is included in a related embodiment is an air (or other gas or other fluid) purge system used to keep the optics clean and potentially reduce pre-sparking on contaminant particles which may be present above the processing line. The air purge technique and option has demonstrated improved instrument robustness in harsh operating environments.

Figure 2:
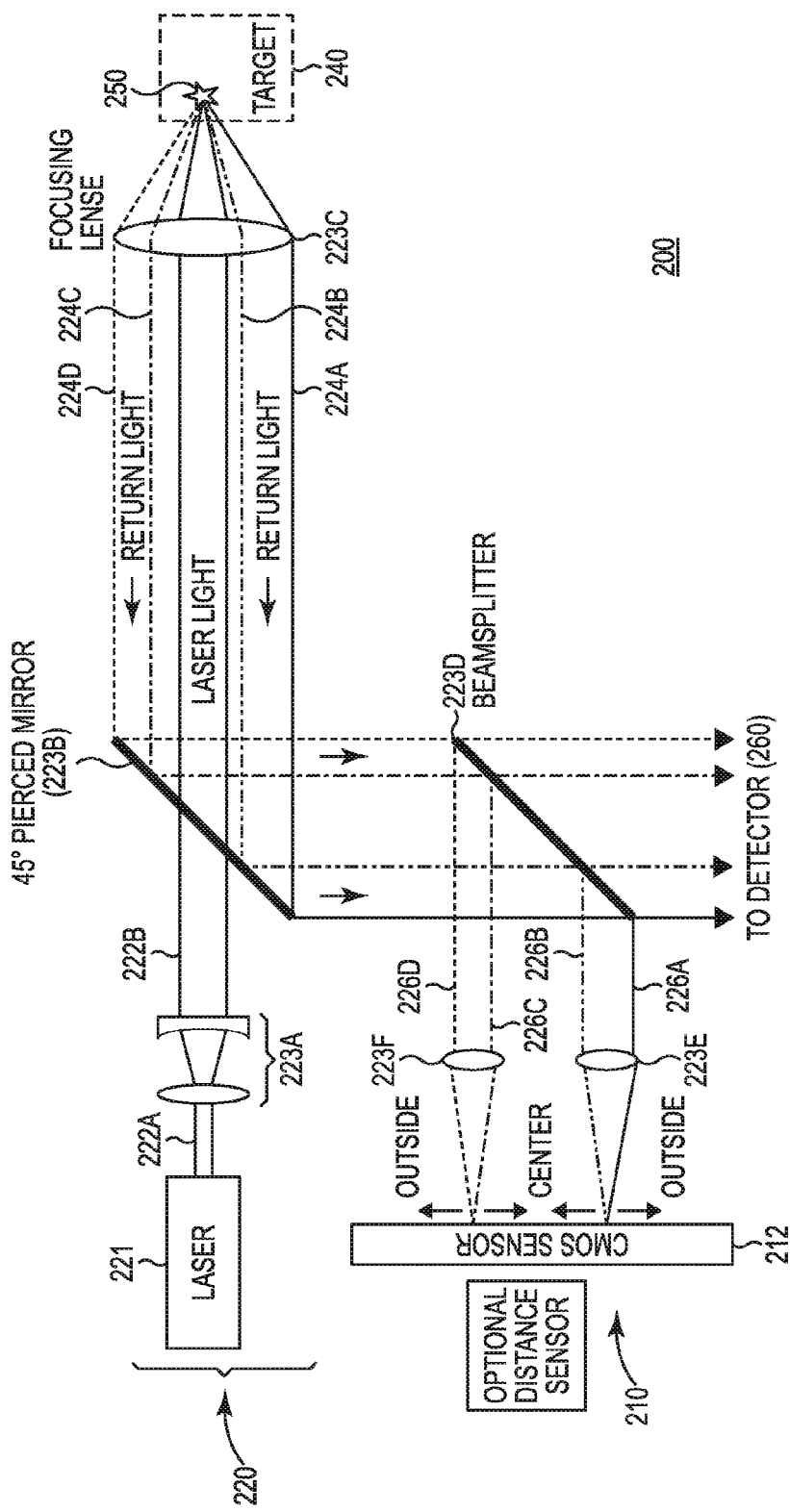
FIG. 2 depicts a schematic of another example embodiment of a laser-based spectroscopy system according to the teachings herein.

Referring now to FIG. 2, there is illustrated an example embodiment of an integrated optical distance sensor assembly 200 using LIBS spectroscopy according to the teachings herein. Sensing system 200 includes a laser-based sensor assembly 220 and an optical distance sensor assembly 210 and, although not shown, also includes a processing unit with a decision algorithm embedded software program for processing return position/distance signals and return laser light signals as described in earlier embodiments. In this example embodiment, laser sensor assembly 220 includes a laser 221 that emits a laser light or beam 222A that passes through an arbitrary set of beam-forming optics 223A (with a ½ inch lens on a fast actuator) forming beam or light 222B that then passes through a hole in a pierced mirror 223B that is angled at a 45 degree angle. Laser light 222B proceeds to be focused on a target 250, which can have a variable distance from a focusing lens 223C. In a related embodiment, target 250 is illuminated by special LED lighting (not shown) of white light or of a pre-selected color to enhance the image of target 250 (where a camera is also used to illuminate an interrogation zone in which target 250 passes).

Return light in the form of beams 224A-224D, in this example embodiment, emanating from target 250 (reflected LED light or natural light) passes through focusing lens 223C and strikes or impinges on a front of the 45° pierced mirror 223B. Reflected return light 224A-224D proceeds to strike or impinge on a beam splitter lens 223D, which is of a specified ratio (e.g. 90-10, 80-20), thereby allowing a specified amount of return light to proceed towards optical distance sensor 210 with the remaining return light proceeding towards a light detector 260. Beam splitter 223D in this example embodiment is a special dichroic beam splitter lens designed to only reflect a particular color range of light corresponding to the color of special LED lights used to illuminate target 250, toward optical distance sensor assembly 210. In this example embodiment, return light 224A-224D are partially reflected from beam splitter 223D as light 226A and 226B, which pass through lens 223E, and light 226C and 226D, which pass through lens 223F. Part of return light 224A-224D passes through beam splitter 223D through to a light detector 260. In one example embodiment, detector 260 is comprised of a lens to capture the return light and an optic fiber on the back side of the lens to direct same to the spectrometer.

With respect to distance sensor 210, lens 223E and 223F form part of distance sensor 210 which also includes an image sensor or CMOS sensor array 212. In particular, the light 226A-226D directed toward optical distance sensor assembly 210 is focused by a pre-configured array of lenses 223E and 223F onto CMOS array 212 (or similar high-speed optical sensor), which is a linear array (oriented vertically in FIG. 2). In a related embodiment, a 2-dimensional CMOS array (oriented with the second dimension into the page in FIG. 2) is used. With respect to linear array 212 and to explain the optical distance sensor operation, by way of a non-limiting example, when target 250 is in the optimum (laser focus) position, the two points of maximum reflected light intensity on the CMOS array will have a maximum at particular focus points as shown in FIG. 2. These points of maximum reflected intensity will move as the target moves in either direction away from the point of optimum positioning. If the target moves away from focusing lens 223C, the return light that is focused on the CMOS array will move toward the center of the array, while if target 250 moves closer to focusing lens 223C, the focused return light on the CMOS array will move toward the outside of array 212.

With such distance/position sensor 210, the position or location of target 250 relative to the optimum focus of laser sensor assembly 220 is rapidly determined. Sensor 210 can be calibrated and the centroid points of maximum intensity would reveal the distance of target 250 from the optimum focus. In one example embodiment, this distance is used to score the relative importance of a detected signal acquired at the same time as the distance to target 250 was measured.

The various embodiments taught herein can be used to measure distance to a target and to measure the distance of the sample from the optimal focus. Other methods would involve modifying systems 100 and 200 to include or substitute for the optical distance sensor an ultrasonic distance sensor or a sensor based on degree of optical focus. Ultrasonic distance sensors are well-known by those skilled in the art. In a related embodiment, the degree of optical focus is assessed from an image (which could be acquired if lenses 223E and 223F in front of CMOS sensor 212 are removed) to which a Fourier Transform (FT) operation is applied. The sharper the image, the more high-frequency components will be observed in the FT operation. In a related embodiment, a continuous laser is added to laser-based spectroscopic sensor assembly 220, collinear with laser 221, such that the reflection of the laser is used to triangulate the position of target 250. Any method of measuring distance from the laser-based sensor instrument/focusing lens to target 150 or 250 is within the purview of the teachings herein.

Other advantages of the laser-based sensing systems described herein are described hereafter. Once the distance from the laser-based sensor instrument to the target is known, a weighting value is assigned to the detected spectroscopic signal that is simultaneously acquired. This weighting value can be determined empirically during calibration of the instrument. This weighting value allows: acquisition of all detected return light signals, with a multiplication factor corresponding to the weighting so as to preferentially select return light signals for which the target is an optimal position; and selective triggering of the Q-switch of a Nd:YAG or similar laser to acquire only signals from the target that are within a particular tolerance in a position or location near the optimal position. Some lasers, such as those used for LIBS or SIBS, have an excitation source, such as a flashlamp or laser diodes, and a Q-switch mode or function that allows the laser light out of the laser cavity at a controlled time. It is often optimal for the laser-based sensor system to run the excitation source of the laser continuously for optimal long term laser performance. In this example embodiment, the Q-switch mode would thus only be triggered on a predetermined distance or distance range of signals predetermined to be "good."

The following patents and publications are incorporated by reference in their entireties: U.S. Pat. Nos. 6,061,641; 6,795,179 and 8,476,545.

The foregoing descriptions present numerous specific details that provide a thorough understanding of various embodiments of the invention. It will be apparent to one skilled in the art that various embodiments, having been disclosed herein, may be practiced without some or all of these specific details. In other instances, components as are known to those of ordinary skill in the art have not been described in detail herein in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention.

For purposes of interpreting the claims for the present invention, it is expressly intended that the provisions of 35 U.S.C. §112, six paragraph, are not to be invoked unless the specific terms "means for" or "step for" are recited in a claim.

What is claimed is:

1. A system for performing laser-based spectroscopic measurements on one or more moving objects within an interrogation zone, comprising:

a laser-based sensor assembly configured to direct a laser light to at least one moving object within the interrogation zone, the laser-based sensor assembly adapted to receive a portion of a set of spectroscopic signals from the at least one moving object;

a position sensor assembly for detecting a position of the at least one moving object within the interrogation zone and for generating position data with an associated weighting factor from the at least one moving object located within the interrogation zone, the weighting factor being a function of a location of the object within the interrogation zone, the weighting factor having a range of zero (0) for no importance to about one (1) for high importance; and a processing unit adapted to receive the set of spectroscopic signals from the laser-based sensor assembly and adapted to receive position data from the position sensor assembly, the processing unit including decision logic therein configured to use the weighted position data to perform weighted selective sorting of the spectroscopic signals received from the at least one moving object as a function of a location of the object within the interrogation zone.

2. The system of claim 1 wherein the processing unit is configured to use the weighted position data to trigger the laser light when the object is within the interrogation zone.

3. The system of claim 2 wherein moving objects within the interrogation zone includes moving the laser-based sensor assembly and interrogation zone relative to the object to be sampled.

4. The system of claim 1 wherein the set of spectroscopic signals are collected when the object is within the interrogation zone or are collected from the object and then are weighted as a function of the location of the object within the interrogation zone.

5. The system of claim 1 wherein the laser light comprises a series of selected laser pulses directed at the object, the spectroscopic signals of which are counted based on the weighted position data of the object.

6. The system of claim 1 further comprising an object handling assembly configured to move the objects through the interrogation zone, the object handling assembly selected from the group consisting of a conveyor, a chute and a tube.

7. The system of claim 1 further comprising a camera and light assembly adapted to illuminate the interrogation zone.

8. The system of claim 1 wherein the position sensor assembly is selected from the group consisting of an optical sensor, an ultrasonic sensor, an infrared sensor and an X-ray sensor.

9. The system of claim 1 further comprising a fluid purge system adapted to clean an optics member of the spectroscopic measurement system.

10. A system for performing laser-based spectroscopic measurements on one or more moving target objects within an interrogation zone comprising:

a laser-based sensor assembly configured to direct a laser light through a focusing lens to at least one moving object within the interrogation zone, the laser-based sensor assembly including a detector assembly adapted to receive a first portion of a set of spectroscopic signals from the at least one moving target object;

a position sensor assembly for detecting a position of the at least one moving target object away from the focusing lens within the interrogation zone and for generating position data with an associated weighting factor from the at least one moving target, wherein the weighting factor is a function of a location of the object away from the focusing lens, the weighting factor having a range of zero (0) for no importance to about one (1) for high importance, the position sensor assembly including a set of lenses adapted to receive and direct a second portion and a third portion of the set of spectroscopic signals to an image sensor array; and a beamsplitter lens member adapted to direct the first portion of the set of spectroscopic signals to the detector assembly, the beamsplitter member further adapted to direct the second and third portions of the set of spectroscopic signals to the lenses and the image sensor array of the position sensor assembly, wherein the second and third portions of the set of spectroscopic signals move toward a center of the image sensor array when the target object moves away from the focusing lens, and wherein the second and third portions of spectroscopic signals move away from the center of the image array when the target object moves closer to the focusing lens.

11. The system of claim 10 further comprising a processing unit adapted to receive the set of spectroscopic signals from the laser-based sensor assembly and adapted to receive position data from the position sensor assembly, the processing unit including decision logic therein configured to use the position data to perform selective sorting of the spectroscopic signals received from the at least one moving target object.

12. The system of claim 10 wherein the detector assembly is comprised of a light collector having one or more optical guides for receiving the first portion of spectroscopic signals and directing them to a spectral analyzer.

13. The system of claim 10 comprises a diode pumped Nd:YAG laser configured to provide a continuous laser beam.

14. The system of claim 10 further comprising a processing unit adapted to receive the position data from the position sensor assembly and adapted to trigger firing of the laser light at the moving object when decision logic of the processing unit determines from the position data that the moving object has a weighting factor below 1 and is at a desired distance from the focusing lens.

15. A system for performing laser-based spectroscopic measurements on one or more moving objects within an interrogation zone comprising:

a laser-based sensor assembly configured to direct a laser light to at least one moving object within the interrogation zone, the laser-based sensor assembly adapted to receive a portion of a set of spectroscopic signals from the at least one moving object upon contact with the laser light;

a position sensor assembly for detecting a position of the at least one moving object within the interrogation zone and for generating position data from the at least one moving object located within the interrogation zone, the weighting factor being a function of a proximity of the object within the interrogation zone, the weighting factor having a range of zero (0) for no proximity to about one (1) for high proximity; and a processing unit adapted to receive the position data from the position sensor assembly and adapted to trigger firing of the laser light at the moving object when a decision logic of the processing unit determines from the position data that the moving object is within, or at high proximity to, the interrogation zone.

16. The system of claim 15 wherein the laser-based sensor assembly adapted to receive a set of spectroscopic signals with high proximity to the interrogation zone from the at least one moving object after the laser light is fired.

17. The system of claim 16 wherein the processing unit is adapted to receive the set of spectroscopic signals from the laser-based sensor assembly and adapted to receive position data from the position sensor assembly, the processing unit including decision logic therein configured to use the position data to perform selective sorting of the spectroscopic signals received from the at least one moving target object as a function of the proximity of the object to the interrogation zone.

18. The system of claim 15 wherein moving objects within the interrogation zone includes moving at least the laser-based sensor assembly and interrogation zone relative to the object to be sampled.

19. The system of claim 15 further comprising an object handling assembly configured to move the objects through the interrogation zone, the object handling assembly selected from the group consisting of a conveyor, a chute and a tube.

20. The system of claim 15 wherein the position sensor assembly is selected from the group consisting of an optical sensor, an ultrasonic sensor, an infrared sensor and an X-ray sensor.

\* \* \* \* \*